United States Patent
Mitchell et al.

(10) Patent No.: US 6,194,631 B1
(45) Date of Patent: Feb. 27, 2001

(54) POLY (VINYLAMINE)-BASED SUPERABSORBENT GELS AND METHOD OF MANUFACTURING THE SAME

(75) Inventors: Michael A. Mitchell, Lake Zurich; Thomas W. Beihoffer, Arlington Heights; Leticia L Trzupek, Hoffman Estates; Jerald W. Darlington, Jr., Marengo; Mark Anderson, Wheaton, all of IL (US)

(73) Assignee: Amcol International Corporation, Arlington Heights, IL (US)

( * ) Notice: Subject to any disclaimer, the term of this patent is extended or adjusted under 35 U.S.C. 154(b) by 0 days.

(21) Appl. No.: 09/179,554

(22) Filed: Oct. 28, 1998

Related U.S. Application Data

(63) Continuation-in-part of application No. 08/974,119, filed on Nov. 19, 1997, now Pat. No. 5,981,689.

(51) Int. Cl.[7] ................ A61F 13/15; C08J 3/00; C08L 3/00
(52) U.S. Cl. ................................ 604/368; 524/521
(58) Field of Search ................ 604/368; 524/521

(56) References Cited

U.S. PATENT DOCUMENTS

| | | | |
|---|---|---|---|
| 3,901,236 | * 8/1975 | Assarsson et al. | 128/284 |
| 4,018,826 | 4/1977 | Gless, Jr. et al. | 260/583 P |
| 4,798,871 | 1/1989 | Lai et al. | 525/328.2 |
| 4,804,793 | 2/1989 | Lai et al. | 574/445 |
| 4,818,598 | 4/1989 | Wong | 428/284 |
| 4,843,118 | 6/1989 | Lai et al. | 524/555 |
| 5,085,787 | 2/1992 | Pinschmidt | 252/8.551 |
| 5,126,395 | 6/1992 | End et al. | 524/801 |
| 5,274,018 | 12/1993 | Tanaka et al. | 524/166 |
| 5,360,420 | * 11/1994 | Cook et al. | 604/378 |
| 5,464,908 | 11/1995 | Sato et al. | 525/380 |
| 5,562,646 | 10/1996 | Goldman et al. | 604/368 |
| 5,599,335 | 2/1997 | Goldman et al. | 604/368 |
| 5,662,781 | 9/1997 | Denzinger et al. | 204/158.21 |
| 5,669,894 | 9/1997 | Goldman et al. | 604/368 |
| 5,797,893 | * 8/1998 | Wada et al. | 604/372 |
| 5,804,605 | 9/1998 | Palumbo | 521/28 |
| 5,843,575 | * 12/1998 | Wang et al. | 428/407 |
| 5,849,405 | * 12/1998 | Wang et al. | 428/304.4 |
| 5,851,672 | * 12/1998 | Wang et al. | 428/407 |
| 5,985,432 | * 11/1999 | Wang et al. | 428/304.4 |

FOREIGN PATENT DOCUMENTS

| | | | |
|---|---|---|---|
| 61 051007 | 3/1986 | (JP) | C08F/8/12 |
| WO 95/26209 | 10/1995 | (WO) . | |
| WO 96/15162 | 5/1996 | (WO) | C08F/20/06 |
| WO 96/15163 | 5/1996 | (WO) | C08F/20/56 |
| WO 96/15180 | 5/1996 | (WO) | C08J/5/02 |
| WO 98/24832 | 6/1998 | (WO) | C08J/3/075 |
| WO 98/37149 | 8/1998 | (WO) | C08L/101/14 |

* cited by examiner

Primary Examiner—John G. Weiss
Assistant Examiner—Paul Shanoski
(74) Attorney, Agent, or Firm—Marshall, O'Toole, Gerstein, Murray & Borun

(57) ABSTRACT

Poly(vinylamine)-based superabsorbent gels are disclosed. The superabsorbent gels either comprise a mixture of a poly(vinylamine) polymer and an acidic water-absorbing polymer, like polyacrylic acid, or comprise a salt of a poly(vinylamine) polymer. An improved method of preparing poly(vinylamine), and improved diaper cores, also are disclosed.

21 Claims, 4 Drawing Sheets

POLY (VINYLAMINE)-BASED SUPERABSORBENT GELS AND METHOD OF MANUFACTURING THE SAME

CROSS-REFERENCE TO RELATED APPLICATIONS

This is a continuation-in-part application of U.S. application Ser. No. 08/974,119, filed Nov. 19, 1997, U.S. Pat. No. 5,981,689.

FIELD OF THE INVENTION

The present invention relates to superabsorbent gels containing a poly(vinylamine), or a salt thereof, and to an improved method of manufacturing a poly(vinylamine). The superabsorbent gels comprise a poly(vinylamine), and preferably a poly(vinylamine) admixed with an acidic superabsorbent polymer, like a polyacrylic acid, or comprise a salt of a poly(vinylamine).

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. No. 5,669,894. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, like a diaper.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers do not function as effective SAPs in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, like urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslink in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, like urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

Prior investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, like polyacrylic acid, and an amount of an ionizable surfactant sufficient to form at least a monolayer of surfactant on the polymer. In another embodiment, a cationic gel, like a gel containing quaternized ammonium groups and in the hydroxide (i.e., OH) form, is used with an anionic gel (i.e., a polyacrylic acid) to remove electrolytes from the solution by ion exchange.

Wong U.S. Pat. No. 4,818,598 discloses admixing a fibrous anion exchange material, like DEAE cellulose, and a hydrogel, like a polyacrylate, to improve absorption properties. WO 96/17681 discloses admixing an anionic SAP, like polyacrylic acid, with a polysaccharide-based cationic SAP to overcome the salt poisoning effect. Similarly, WO 96/15163 discloses admixing a cationic SAP having at least 20% of the functional groups in a basic (i.e., OH) form with a cationic exchanges resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect. It would be desirable, however, to provide an SAP that exhibits exceptional absorbency and retention, like a sodium polyacrylate, and, therefore, can be used alone as an SAP. It also would be desirable to admix such an SAP with polyacrylic acid, or another acid-containing SAP, to overcome the salt poisoning effect.

SUMMARY OF THE INVENTION

The present invention is directed to poly(vinylamine)-based superabsorbent gels. A poly(vinylamine) polymer can be used in conjunction with an acidic water-absorbing resin, like polyacrylic acid, to help overcome the salt poisoning effect, or a salt of a poly(vinylamine) polymer can be used alone as an SAP. The poly(vinylamine) polymer also can be used, alone, as an SAP to absorb and retain acidic media. More particularly, the poly(vinylamine) used as an SAP, or as a component of an SAP, is lightly crosslinked and, in preferred embodiments, is surface treated to improve absorption properties.

Accordingly, one aspect of the present invention is to provide an improved method of manufacturing a poly(vinylamine) comprising vinylamine monomer units, and which can be crosslinked using a suitable polyfunctional vinyl monomer. The present method substantially reduces the amount of residual N-vinylamide monomer in the poly(N-vinylamide) precursor of the poly(vinylamine), and, therefore, eliminates the stringent purification procedures, or reduces the long polymerization reaction times, previously used to overcome the problem of residual monomer content. Consequently, the present improved process reduces process time and production costs.

Another aspect of the present invention is to provide an SAP having absorbency and retention properties comparable to a conventional SAP, like sodium polyacrylate. A present SAP is produced by neutralizing a poly(vinylamine) with a sufficient amount of acid, like hydrochloric acid, such that at least about 10%, i.e., about 10% to 100%, of the amine-functional groups are neutralized. The resulting poly(vinylamine) salt is an excellent SAP for absorbing aqueous media.

In accordance with another important aspect of the present invention, a lightly crosslinked poly(vinylamine), alone and unneutralized, can be used to absorb and retain acidic aqueous media. The acidic aqueous media converts the low-absorbing poly(vinylamine) to a highly absorbing poly(vinylamine) salt, i.e., converts the polymer to an SAP, during absorption. A poly(vinylamine), therefore, is an excellent resin for cleaning acid spills and the remediation of acidic species.

Yet another aspect of the present invention is to provide an improved SAP that overcomes the salt poisoning effect of electrolytes. In particular, the improved SAP material contains a mixture of an acidic swellable resin, like polyacrylic acid, and a poly(vinylamine).

These and other aspects and advantages of the present invention will become apparent from the following detailed description of the preferred embodiments.

DETAILED DESCRIPTION OF THE PREFERRED EMBODIMENTS

Figure 1:
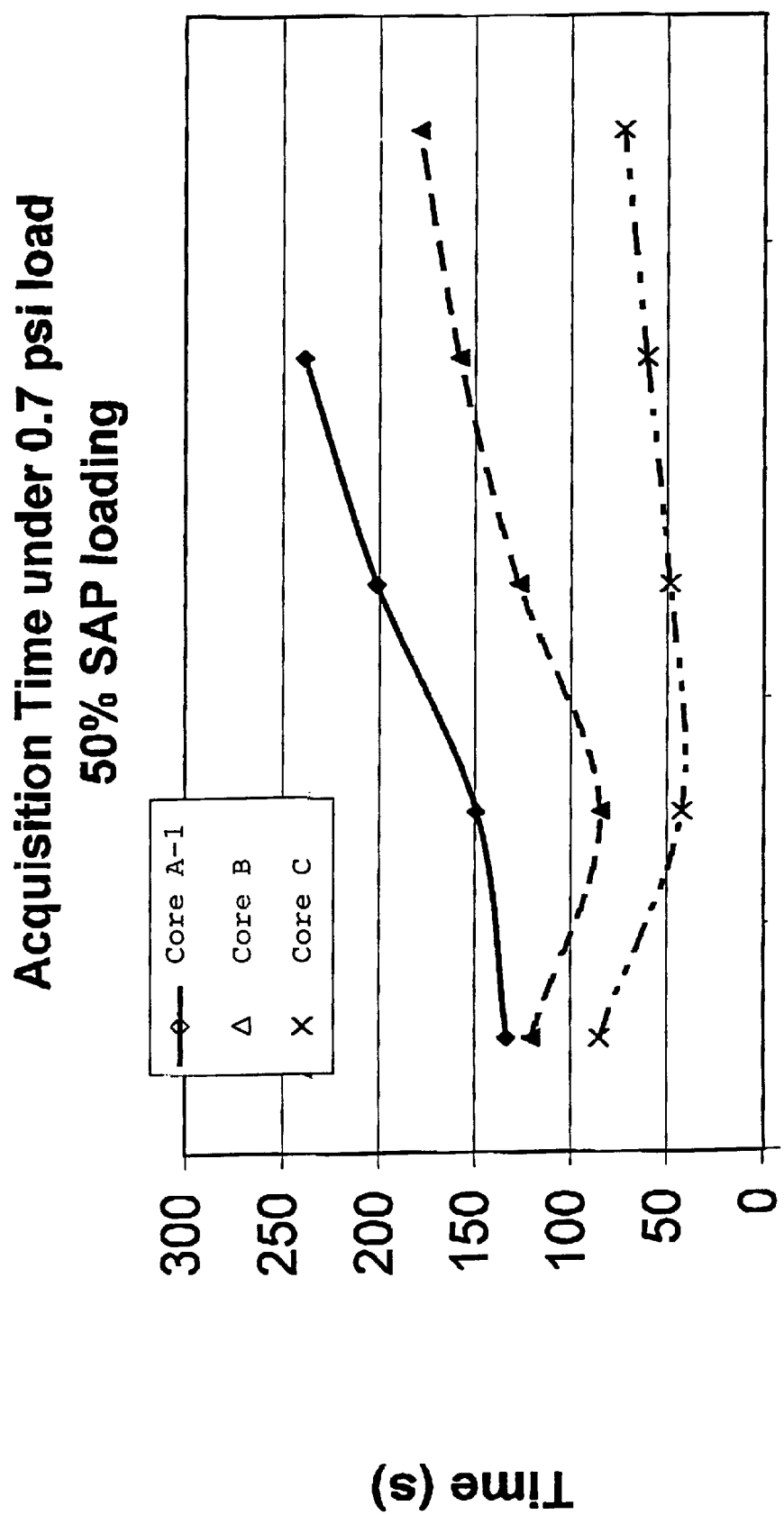
FIGS. 1 and 2 are plots of acquisition time (seconds) vs. number of insults for a series of laboratory prepared diaper cores under a load of 0.7 psi.

The present invention is directed to: (a) an improved method of manufacturing poly(vinylamine), (b) poly(vinylamine) and poly(vinylamine) salts and their use as SAPs, and (c) an improved SAP material comprising an admixture of a poly(vinylamine) and an acidic water-absorbing resin. (a) An Improved Method of Manufacturing Poly(vinylamine)

Poly(vinylamine), and salts derived therefrom, are known polymers. For example, the following patents disclose the synthesis or manufacture of poly(vinylamine): U.S. Pat. No. 4,798,871; U.S. Pat. No. 4,843,118; and U.S. Pat. No. 4,804,793. In addition, U.S. Pat. No. 4,018,826 discloses a process for preparing poly(vinylamine) and salts thereof. Ford et al. U.S. Pat. No. 5,491,199 discloses the preparation of formate-free poly(vinylamine) by heating the polymer in the presence of transition metal catalyst.

The above patents generally disclose polymers of N-vinylformamide that subsequently are hydrolyzed. Upon hydrolysis, the poly(N-vinylformamide) is converted into a poly(vinylamine). Hydrolysis can be performed under acid or basic conditions. The cationic charge on the resulting vinylamine, i.e., the charge density, is related to the pH of the medium. At a low pH, the poly(vinylamine) is protonated and has a high cationic charge density. Conversely, at a high pH, the poly(vinylamine) is not protonated, and the polymer has a substantially reduced cationic charge density, if any.

In general, an uncrosslinked poly(vinylamine) is a water-soluble polymer that has many practical applications, such as in water treatment, personal care products, and ion exchange resins. Poly(vinylamine) is rendered water insoluble by a crosslinking the polymer. Although polyvinylamines, and salts thereof, are well known, it has not heretofore been suggested that such polymers can be used as an SAP.

Typically, a poly(vinylamine) polymer is produced by hydrolysis of poly(N-vinylformamide), under either acid or basic conditions. Poly(vinylamine) also can be produced from other poly(N-vinylamides), like poly(N-vinylacetamide), poly(N-vinylpropionamide), and poly(N-vinylsuccinamide). It is desirable that hydrolysis of the poly(vinylamide) is substantially to essentially complete, i.e., about 10% to 100% complete, and preferably about 30% to 100% complete. To achieve the full advantage of the present invention, at least about 50%, and more preferably at least about 90%, of the amide groups are hydrolyzed to an amine functionality. The amine-functional polymer can contain other copolymerizable units, i.e., other monoethylenically unsaturated monomers, as long as the polymer is substantially, i.e., at least 10%, and preferably at least 25%, vinylamine units. To achieve the full advantage of the present invention, the polymer contains at least 50%, and more preferably at least 75%, vinylamine units.

If residual monomer or other impurities are present in the poly(vinylamide), hydrolysis conditions can lead to a crosslinking, which increases the molecular weight of the poly(vinylamine) and can result in undesirable and unpredictable gel formation. Therefore, current methods of synthesizing poly(vinylamine) require either a rigorous purification of the poly(N-vinylformamide), or an extremely long reaction time and a relatively high reaction temperature to ensure that all the residual poly(N-vinylformamide) monomer is consumed during the polymerization.

The production of poly(vinylamine) would be facilitated, and production costs decreased, by an improved method of removing residual N-vinylamide monomers from the poly (N-vinylamide). Therefore, in accordance with an important feature of the present invention, an improved method of manufacturing poly(vinylamine) is disclosed.

As set forth above, polymerization of N-vinylformamide, followed by hydrolysis, is the most common method of producing poly(vinylamine). The polymerization can be performed in the presence or absence of a crosslinker, i.e., a polyfunctional organic compound. However, residual N-vinylformamide monomer, or other monomer impurities, like aldehydes, can cause crosslinking and undesired gel formation during hydrolysis. In accordance with an important feature of the present invention, it has been found that the problem of residual monomer content, and the presence of other impurities, can be overcome by the use of suitable scavenging agents to remove the residual monomer and other impurities from the poly(N-vinylamide). The use of scavenging agents has the advantage of greatly reducing the process time, and costs, currently invested to insure that all the N-vinylamide monomer and other impurities are consumed prior to hydrolysis.

In accordance with an important feature of the present invention, a scavenging agent is added to a poly(N-vinylamide), prior to hydrolysis, in an amount of about 0.1% to about 3%, and preferably about 0.1% to about 2%, by weight, based on the weight of N-vinylamide monomer used in the polymerization. To achieve the full advantage of the present invention, the scavenging agent is added in an amount of about 0.1% to about 1%, by weight, based on the weight of N-vinylamide monomer.

The scavenging agent can be any compound capable of reacting with N-vinylamides, like N-vinylformamide, and other aldehydic impurities, like formaldehyde or acetaldehyde, under hydrolysis conditions, i.e., a temperature of about 25° C. to about 80° C. for about 4 to about 24 hours in the presence of an acid or a base. Typically, a scavenging agent is capable of reacting with an aldehyde in about 1 minute to about 10 minutes at a temperature of about 20° C. to about 80° C.

Examples of scavenging agents include, but are not limited to: (a) oxidizing agents, like potassium permanganate, ammonia silver salts (Tollen's Reagent), potassium dichromate, and hydrogen peroxide; (b) reducing agents, like catalytic hydrogenation, lithium aluminum hydride, sodium borohydride, diborane, aluminum hydride, LiAlH (O.t-Bu)$_3$ (lithium aluminum tri-t-butoxy hydride), LiAlH-(OCH$_3$)$_3$ (lithium aluminum trimethoxy hydride), zinc (mercury) and concentrated hydrochloric acid, and hydrazine and a base; (c) Grignard reagents, like aryl and alkyl magnesium halides; (d) sodium or potassium cyanide with sodium bisulfite; (e) sodium bisulfite; and (f) ammonia derivatives, like hydroxylamine, hydrazine, substituted hydrazines, e.g., phenyl hydrazine, and semicarbazine. A reducing agent is a preferred scavenging agent, and sodium borohydride is a most preferred scavenging agent. Such scavenging agents have the advantages of being inexpensive, greatly reducing the reaction time to form a poly(N-vinylamide), and eliminating the need to purify the poly(N-vinylamide).

To achieve the full advantage of the present invention, the scavenging agent is an aqueous solution containing sodium borohydride, e.g., about 10% to about 15% by weight, and sodium hydroxide. The sodium borohydride acts quickly, is highly effective, and is inexpensive. As an added advantage, the sodium hydroxide is useful in a subsequent basic hydrolysis of the poly(N-vinylamide). Prior to hydrolyzing the poly(N-vinylamide), the poly(N-vinylamide) and scavenging agent are held at about 25° C. to about 80° C. for about 1 minute to about 10 minutes to eliminate essentially all, i.e., about 95% to 100%, of the residual monomers and impurities.

After using a scavenging agent to remove residual monomers and other impurities, the poly(N-vinylamide) is hydrolyzed. The amount of acid or base used to hydrolyze the poly(N-vinylamide) in solution can vary widely, and is generally added in a molar ratio of acid or base to N-vinylamide monomer content of the initially formed polymer of about 0.05:1 to about 3:1, preferably of about 0.3:1 to about 1:1. To achieve the full advantage of the present invention, the molar ratio of acid or base to N-vinylamide monomer is about 0.7:1 to about 1:1.

Generally, hydrolysis is achieved with a suitable acid, such as an inorganic acid, for example, hydrochloric acid, hydrobromic acid, hydrofluoric acid, sulfuric acid, nitric acid, phosphoric acid, and the like. In addition, suitable bases, such as an inorganic base, for example, sodium hydroxide, ammonia, ammonium hydroxide, potassium hydroxide, and the like, can also be used. Hydrolysis is conducted at a temperature of about 25° C. to about 100° C. for about 4 to about 24 hours.

The degree of hydrolysis is controlled by the amount of acid or base, the reaction temperature, and/or the reaction time. In general, greater amounts of acid or base, higher reaction temperatures, and longer reaction times result in higher degrees of hydrolysis.

The present method, therefore, is an improved method of manufacturing either crosslinked or uncrosslinked poly (vinylamine). The following examples illustrate the improved method in the manufacture of uncrosslinked poly (vinylamine).

EXAMPLE 1

N-vinylformamide (400 g, 5.6 mole) was dissolved in 3,000 g of deionized water, then the resulting monomer solution was sparged with argon for one hour. In a separate vessel, 5 g of 2,2'-azobis(2-amidinopropane)hydrochloride initiator (i.e., V-50 initiator available from Wako Pure Chemical Industries, Inc., Osaka, Japan) was dissolved in 70 g of deionized water, then the resulting initiator solution was sparged with argon for one-half hour. A 7 g portion of the initiator solution was added to the monomer solution, and the remainder of the initiator solution was added to the monomer solution over an hour period while heating the resulting reaction mixture to about 45° C. The reaction temperature was maintained at about 45° C. for about 4 hours. The reaction mixture then was heated to 55° C. and held for two hours. Finally, 20 g of a 15% by weight aqueous V-50 solution was added to the reaction mixture, and the polymerization reaction was held at 65° C. for 12 hours to provide poly(N-vinylformamide).

The aqueous poly(N-vinylformamide) solution then was heated to about 70° C., while 20 g of a 12% by weight sodium borohydride solution (in 41% aqueous sodium hydroxide) was added to the polymer solution. After the scavenger solution was added, 480 g of 50% aqueous sodium hydroxide was added to the polymer solution, and the resulting solution was stirred for about 8 hours at about 70° C. to hydrolyze the poly(N-vinylformamide).

If desired, the resulting poly(vinylamine) solution then can be purified by ultrafiltration. In this optional purification, the poly(vinylamine) solution was diluted with 3 liters of deionized water. The diluted solution then was ultrafiltered with a 100,000 molecular weight cut-off tangential flow ultrafiltration module. The diluted polymer solution was washed with 25 liters of deionized water, and then concentrated to 2,500 ml to give a 4 wt% solution of sodium formate-free poly(vinylamine).

Example 1 was repeated, but the scavenger step using sodium borohydride was omitted. During hydrolysis, the aqueous solution of poly(N-vinylformamide) gelled. Gelling was attributed to impurities present in the N-vinylformamide monomer that were not removed in a scavenging step.

The following example illustrates the ability of a scavenger, like sodium borohydride, to reduce the reaction time in the synthesis of a poly(vinylamine).

EXAMPLE 2

A five liter flask was charged with 400 g of N-vinylformamide monomer and 2,970 g of deionized water, and the resulting monomer solution was sparged with argon for one hour. Separately, an initiator solution was prepared by dissolving 5 g of V-50 in 67 g of deionized water, and sparging with argon for 0.5 hours. A portion of the initiator solution (7 g) was added to the monomer solution. The remainder of the initiator solution was added to the monomer solution over a one-hour time period, while the resulting reaction mixture was heated to 45° C. The reaction mixture was held at 45° C. for 2.5 hours, then heated to 55° C. and held for an additional 2.5 hours, and finally heated to 65° C. and held for an additional one hour. Next, 20 g of 12% sodium borohydride in a 41% aqueous sodium hydroxide solution was added to the reaction mixture, followed immediately by 480 g of a 50% aqueous sodium hydroxide solution. The reaction mixture quickly turned pink in color but then returned to colorless. The hydrolysis step was continued at 70° C. for an additional 8 hours. The resulting poly(vinylamine) solution can then be purified, if desired, by ultra-filtration as set forth in Example 1. In the absence of a sodium borohydride scavenger, the reaction requires an additional several hours to react all the N-vinylformamide monomers and other impurities, as set forth in Example 1.

EXAMPLE 3

Freshly distilled N-vinylformamide (250 g, 3.5 mole) and 2.8 g of 15% V-50 initiator were dissolved in 400 g of deionized water, then the resulting reaction solution was sparged with argon for 15 minutes. Next, the reaction solution was poured into a glass pan and cured at 15 mW/cm$^2$ of UV light for 25 minutes. The polymerization was exothermic, eventually reaching about 100° C. The resulting concentrated poly(N-vinylformamide) solution was very viscous.

The concentrated poly(N-vinylformamide) solution (312 g) then was diluted with 2 liters of deionized water, and the diluted polymer solution was heated to 70° C. Six (6) g of a sodium borohydride solution (15% by weight of 41% aqueous sodium hydroxide) was added dropwise to the heated polymer solution over a five-minute time period, followed by the addition of 143 g of 50% aqueous sodium hydroxide. The resulting solution was maintained at 70° C. for 8 hours to hydrolyze the poly(N-vinylformamide), then cooled and purified as in Example 1.

The present improved method of manufacturing poly (vinylamine) also can be used in processes wherein poly (vinylamine) is derived from, for example, poly(N-vinylacetamide), poly(N-vinylpropionamide), poly(N-vinylsuccinamide), and similar N-vinylcarboxamides.

The present improved method of manufacturing a poly (vinylamine) can also be used in the manufacture of a crosslinked poly(vinylamine). As described above, SAPs are crosslinked to a sufficient extent such that the polymer is water insoluble. Crosslinking serves to render the poly (vinylamine) polymers substantially water insoluble, and, in part, serves to determine the absorptive capacity of the polymers. For use in absorption applications, the poly (vinylamine) is lightly crosslinked, i.e., has a crosslinking density of less than about 20%, and preferably less than about 10%, and most preferably about 0.01% to about 7%.

When used, a crosslinking agent most preferably is included in an amount of less than about 7 wt %, and typically about 0.1 wt % to about 5 wt %, based on the total weight of monomers. A poly(vinylamine) can be crosslinked by two different pathways. One pathway utilizes olefinically unsaturated crosslinking monomers that copolymerize with the N-vinylamide, and, therefore, form a part of the polymeric backbone. The crosslinked poly(N-vinylamide) then is hydrolyzed to provide crosslinked polyvinylamine.

Examples of crosslinking polyvinyl monomers include, but are not limited to, polyacrylic (or polymethacrylic) acid esters represented by the following formula (I); and bisacrylamides, represented by the following formula (II).

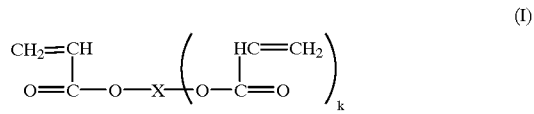

(I)

wherein x is ethylene, propylene, trimethylene, hexamethylene, 2-hydroxypropylene, —(CH$_2$CH$_2$O)$_n$—CH$_2$CH$_2$—, or

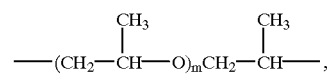

n and m are each an integer 5 to 40, and k is 1 or

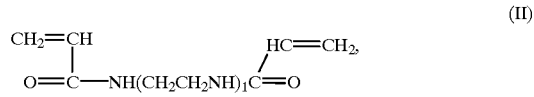

(II)

wherein l is 2 or 3.

The compounds of formula (I) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (II) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimelhacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides or mixtures thereof. Compounds like divinylbenzene and divinyl ether also can be used to crosslink the poly(N-vinylamide). Especially preferred crosslinking agents are N,N'-methylenebisacrylamide, N,N'-methylenebismethacrylamide, ethylene glycol dimethacrylate, and trimethylolpropane triacrylate.

The following example illustrates a crosslinked poly(vinylamine) prepared in accordance with the present invention.

EXAMPLE 4

A monomer mixture containing N-vinylformamide (250 grams), deionized water (250 grams), methylenebisacrylamide (1.09 grams), and V-50 initiator (0.42 grams) was placed in a shallow dish, then polymerized under an ultraviolet lamp as set forth in Example 3 until the mixture polymerized into a rubbery gel. The concentrated poly(N-vinylformamide) then was treated with a sodium borohydride/sodium hydroxide solution, as set forth in Example 1, to yield a lightly crosslinked poly(vinylamine). Sodium formate present in the crosslinked poly(vinylamine) can be removed by washing the resin with acetone/water mixtures, or by other suitable methods known to persons skilled in the art.

Poly(vinylamine) also can be crosslinked in solution by suspending or dissolving uncrosslinked poly(vinylamine) in an aqueous medium, then adding a di- or poly-functional compound capable of crosslinking the poly(vinylamine) by reaction with the amino groups of the polymer. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $WS(O_2)O—(CH_2)_n—OF(O)_2W$, wherein n is one to 10, and W is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate). Crosslinking agents also are disclosed in Pinschmidt, Jr. et al. U.S. Pat. No. 5,085,787, incorporated herein by reference, and in EP 450 923.

In general, the crosslinking agent should be water soluble and possess sufficient reactivity with poly(vinylamine) such that crosslinking occurs in a controlled fashion, preferably at a temperature of about 25° C. to about 150° C. A preferred crosslinking agent is ethylene glycol diglycidyl ether (EGDGE), a water-soluble diglycidyl ether.

The following example illustrates light crosslinking of a sodium formate-free poly(vinylamine) of the present invention using a polyfunctional crosslinking agent that reacts with the amino groups of the polymer.

EXAMPLE 5

To 2 liters of a 3% by weight aqueous poly(vinylamine) solution was added 0.18 g of ethyleneglycol diglycidyl ether (EGDGE). The resulting mixture was stirred to dissolve the EGDGE, then the mixture was heated to about 60° C. and held for one hour to gel. The gel was heated to about 80° C. and held until about 90% of the water was removed. The resulting gel then was extruded and dried to a constant weight at 80° C. The dried, lightly crosslinked poly(vinylamine) then was cryogenically milled to form a granular material capable of absorbing water or acid solutions. The gel exhibited the following absorption characteristics in 0.1 M hydrochloric acid (HCl):

$AUNL^{1)}$=59.3 g/g $AUL^{2)}$ (0.28 psi)=37.8 g/g $AUL^{2)}$ (0.7 psi)=26.4 g/g

[1] Absorption under no load; and
[2] Absorption under load.

Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g +/−0.001 g) is carefully scattered onto a 140-micron, water-permeable mesh attached to the base of a hollow plexiglass cylinder with an internal diameter of 25 mm. The sample is covered with a 100 g cover plate and the cylinder assembly weighed. This gives an applied pressure of 20 g/cm² (0.28 psi). Alternatively, the sample can be covered with a 250 g cover plate to give an applied pressure of 51 g/cm² (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact. As discussed hereafter, the poly(vinylamine) particles also can be surface treated with a crosslinking agent, like ethyleneglycol diglycidyl ether, to give an absorbent having improved performance under external pressure.

In a preferred embodiment, a lightly crosslinked poly(vinylamine) is subjected to a process step wherein the surface of the poly(N-vinylamine) is further crosslinked. It has been found that surface crosslinking of a poly(vinylamine) enhances the ability of the polymer to absorb and retain aqueous media under load.

Surface crosslinking is achieved by spraying poly(vinylamine) particles with an isopropyl alcohol solution of a surface crosslinking agent to wet predominantly only the outer surfaces of the poly(vinylamine) particles. Surface crosslinking and drying of the polymer then is performed, preferably by heating at least the wetted surfaces of the poly(vinylamine) particles.

Typically, the poly(vinylamine) particles are surface treated with an alcoholic solution of a surface crosslinking agent. The particles can be in the form of granules, a foam, beads, flakes, fibers, or powders, for example. The solution contains about 0.01% to about 4%, by weight, surface crosslinking agent, and preferably about 0.4% to about 2%, by weight, surface crosslinking agent in a suitable solvent. The solution can be applied as a fine spray onto the surface of freely tumbling poly(vinylamine) particles at a ratio of about 1:0.01 to about 1:0.5 parts by weight poly(vinylamine)

to solution of surface crosslinking agent. The surface crosslinker is present in an amount of 0% to about 1%, by weight of the poly(vinylamine), and preferably 0% to about 0.5% by weight. To achieve the full advantage of the present invention, the surface crosslinker is present in an amount of about 0.001% to about 0.1% by weight.

The crosslinking reaction and drying of the surface-treated poly(vinylamine) particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the poly(vinylamine) particle, and any other method of drying the poly(vinylamine) particles, such as microwave energy, or the like, can be used.

Suitable surface crosslinking agents include the di- or poly-functional molecules capable of reacting with amino groups and crosslinking poly(vinylamine). Preferably, the surface crosslinking agent is alcohol or water soluble and possesses sufficient reactivity with a poly(vinylamine) such that crosslinking occurs in a controlled fashion at a temperature of about 25° C. to about 150° C.

Nonlimiting examples of suitable surface crosslinking agents include:

(a) dihalides and disulfonate esters, for example, compounds of the formula $$Z\text{—}(CH_2)_p\text{—}Z$$

wherein p is a number from 2 to 12, and Z, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, like epichlorohydrin;;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and poly-carboxylic acids containing two to twelve carbon atoms, and the methyl and ethyl esters, acid chlorides, and anhydrides derived therefrom, like oxalic acid, adipic acid, succinic acid, dodecanoic acid, malonic acid, and glutaric acid, and esters, anhydrides, and acid chlorides derived therefrom;

(g) organic titanates, like TYZOR AA, available from E.I. DuPont de Nemours, Wilmington, Del.;

(h) melamine resins, like the CYMEL resins available from Cytec Industries, Wayne, N.J.;

(i) hydroxymethyl ureas, like N,N'-dihydroxymethyl-4,5-dihydroxyethylene urea; and (j) multifunctional isocyanates, like toluene diisocyanate, isophorone diisocyanate, xylene diisocyanate, and hexamethylene diisocyanate.

A preferred surface crosslinking agent is ethylene glycol diglycidyl ether (EGDGE), which is a water-soluble diglycidyl ether which crosslinks poly(vinylamine) at a temperature of about 25° C. to about 150° C.

The following Example 6 illustrates surface treatment and crosslinking of a lightly crosslinked poly(vinylamine).

EXAMPLE 6

Divinylbenzene crosslinker (1.085 g, 55% active, by weight, in styrene/ethylstyrene), aqueous V-50 initiator (2.541 g, 15%), and N-vinylformamide (245 g, 3.45 moles) were mixed in 350 g of deionized water. The resulting solution was sparged with argon for 15 minutes, and then polymerized under UV light (15 mW/cm$^2$) for one hour. The resulting gel was extruded, dried at 100° C., and milled to produce particles of lightly crosslinked poly(vinylamine).

A portion of the poly(N-vinylformamide) particles (82 g) was hydrolyzed by dispersing the particles in a solution containing 168 g cyclohexane, 112 g 1-butanol, and 46 g of powdered sodium hydroxide. The resulting suspension then was heated at about 70° C. for about 6 hours. Next, 150 g of deionized water was added to the suspension, and the organic solvents were decanted. Acetone (230 g) then was added to collapse the gel and remove the sodium formate by-product. The water/acetone wash was repeated three more times, and the gel was dried then remilled. The resulting poly(vinylamine) gel then was surface treated with ethylene glycol diglycidyl ether at various levels, and dried at 145° C. to provide a surface crosslink.

The poly(vinylamine) then was tested for an ability to absorb and retain 0.1 M hydrochloric acid.

TABLE 1

| Surface crosslink Level (ppm)[3] | AUNL[1] and AUL[2] (0.1 M HCl) | | |
|---|---|---|---|
| | No Load | 0.28 psi | 0.7 psi |
| 0 | 51 | 23 | 9.9 |
| 100 | 47 | 27 | 19 |
| 500 | 47 | 27 | 19 |
| 1000 | 46 | 28 | 20 |
| 2000 | 41 | 26 | 20 |

[3]ppm--parts per million of surface crosslinker.

The absorption data shows that surface crosslinking substantially improves the absorption under load of a poly (vinylamine), especially at a load of 0.7 psi.

(b) Poly(vinylamine)-Based SAPs

Poly(vinylamine) typically does not function as an SAP in its neutral form because there is no ionic charge on the polymer. The driving force for water absorption and retention therefore is lacking. However, when converted to a salt, or used in conjunction with an acidic water-absorbing resin, like a polyacrylic acid, a poly(vinylamine) then behaves likes an SAP. It should be understood that a poly (vinylamine) produced either by the above-described improved method, or by a prior, conventional method, can be used in a poly(vinylamine)-based SAP.

(i) Salts of Poly(vinylamine)

As previously discussed, sodium poly(acrylate) is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

Poly(vinylamine) is a neutral polymer, and, accordingly, does not possess the polyelectrolytic properties necessary to provide an SAP. However, poly(vinylamine) salts have polyelectrolytic properties sufficient to provide an SAP. The poly(vinylamine) used to provide an SAP is a lightly crosslinked poly(vinylamine), and preferably is surface crosslinked, as set forth above.

Such lightly crosslinked, and optionally surface crosslinked, poly(vinylamine) polymers are converted into salts by methods known in the art. For example, the preparation of poly(vinylamine HCl) by the addition of hydrochloric acid to a poly(vinylamine) is set forth in Pinschmidt, Jr. et al. U.S. Pat. No. 5,085,787, and in Gless, Jr. et al. U.S. Pat. No. 4,018,826, or by hydrolysis of a poly(N-vinylamide) with hydrochloric acid.

A poly(vinylamine) salt useful as an SAP, however, is not limited to the hydrochloride salt. Poly(vinylamine) can be reacted with a variety of acids to provide a poly(vinylamine) salt useful as an SAP, but the preferred acids are mineral acids. To achieve the full advantage of the present invention, the poly(vinylamine) salt is a hydrochloride salt.

To demonstrate the ability of a poly(vinylamine) salt to act as an SAP, the lightly crosslinked poly(vinylamine) of Example 5 was converted to the hydrochloride salt by methods well known in the art. The poly(vinylamine) salt was tested for its ability to absorb and retain deionized water and electrolyte-containing aqueous media (i.e., 0.9% by weight aqueous sodium chloride).

In particular, poly(vinylamine) samples, as prepared in Example 5, were converted to the hydrochloride salt using different amounts of 1N hydrochloric acid (HCl). The resulting gels of poly(vinylamine) salt then were dried and evaluated for an ability to absorb a 0.9% by weight aqueous NaCl solution. The results are summarized in Table 2.

TABLE 2

| Mole % HCL[4] | AUNL[1] | AUL[2] (0.28 psi) | AUL[2] (0.7 psi) |
|---|---|---|---|
| 0 | 18.7 | 13.7 | 12.6 |
| 30 | 31.6 | 21.5 | 15.9 |
| 50 | 39.8 | 25.6 | 20.1 |
| 70 | 43.0 | 23.4 | 13.5 |
| 100 | 28.5 | 9.1 | 9.5 |

[4]mole % HCl added to the poly(vinylamine) based on the moles of N-vinylformamide monomer used to prepare the poly(vinylamine).

The absorbency results summarized in Table 2 show that absorbency increases dramatically, both under load and under no load, when the poly(vinylamine) is converted to a hydrochloride salt, especially in the range of about 30 to about 70 mole % conversion to the salt. In accordance with an important feature of the present invention, a poly(vinylamine) exhibits the properties of an SAP when converted to a salt in an amount of about 10 to about 100, and preferably about 20 to about 90, mole percent. To achieve the full advantage of the present invention, the poly(vinylamine) is converted to a salt in an amount of about 25 to about 75 mole %, based on the weight of N-vinylamide monomer used to prepare the poly(vinylamine).

In another test, a lightly crosslinked poly(vinylamine), as prepared in Example 6, was surface treated with various levels of ethylene glycol diglycidyl ether (EGDGE) in isopropyl alcohol, followed by drying and curing at 80° C. The surface crosslinked granules of lightly crosslinked polyvinylamine then were partially neutralized (i.e., 50 mole %) with 1N HCl. The surface crosslinked polyvinylamine salt, then was tested for an ability to absorb and retain a 0.9% aqueous NaCl solution. The results are summarized in Table 3, and show that a neutralized and surface crosslinked poly(vinylamine) shows an improvement in AUL.

TABLE 3

| Surface crosslink Level of EGDGE (ppm)[4] | AUNL[1] | AUL[2] (0.28 psi) | AUL[2] (0.7 psi) |
|---|---|---|---|
| 0 | 35.8 | 16.6 | 9.3 |
| 100 | 35.3 | 18.9 | 11.3 |
| 500 | 31.5 | 16.3 | 11.2 |
| 1000 | 31.3 | 17.8 | 11.5 |
| 2000 | 28.8 | 18.0 | 11.9 |

(ii) Poly(vinylamine) in SAPs

As illustrated above, poly(vinylamine), in its free base form, does not function as an SAP for neutral-to-basic aqueous media. Similarly, polyacrylic acid, in its free acid form, does not function as an SAP for neutral-to-acidic aqueous media. In each case, the polymer has a low charge density, and, accordingly, a major driving force for absorption and retention, i.e., electrostatic repulsion, is missing. In contrast, partially neutralized polyacrylic acid has a sufficient charge density, and is currently used as an SAP by itself. Similarly, as disclosed above, poly(vinylamine) salts have a high charge density and are excellent SAPs.

However, a poly(vinylamine), in its free base form, can act as an absorbent for acidic aqueous media, i.e., media having a pH less than 7, as illustrated in Examples 5 and 6, wherein one gram of poly(vinylamine) absorbed 59.3 g and 51 g of 0.1 M hydrochloric acid under no load, respectively. The acidic media protonates the amino groups of the poly (vinylamine), thereby providing sufficient charge density for the protonated poly(vinylamine) to perform as an SAP. Accordingly, poly(vinylamine), by itself, can be used to absorb acidic aqueous media, for example, to absorb an acid spill.

It also has been found that poly(vinylamine) polymers, in their free base form, are useful components in superabsorbent materials further containing an acidic water-absorbing resin. For example, a superabsorbent material of the present invention is an admixture of a poly(vinylamine) and an acidic water-absorbing resin, like polyacrylic acid. The present superabsorbent materials are particularly useful with respect to absorbing and retaining aqueous media containing electrolytes.

Currently, superabsorbent materials containing two absorbing components, i.e., bi-component SAP materials, are being investigated as an improved class of SAPs. Typically, one component is a water-absorbing resin, and the second component acts in an ion exchange capacity to remove electrolytes from an aqueous media.

In contrast, the present invention is directed to a bi-component SAP material comprising two uncharged, slightly crosslinked polymers, each of which is capable of swelling and absorbing aqueous media. When contacted with water, the two uncharged polymers neutralize each other to form a superabsorbent material. Neither polymer in its uncharged form behaves as an SAP by itself when contacted with water. The present bi-component superabsorbent material, therefore, contains two resins, one acidic and one basic, which are capable of acting as an absorbent material in their polyelectrolyte form. While polyacrylic acid is an excellent choice for the acidic resin, until the present invention, there has not been an adequate basic resin.

Therefore, in accordance with an important feature of the present invention, poly(vinylamine) is used as the basic resin for a bi-component SAP material. The poly (vinylamine) is lightly and the poly(vinylamine) particles preferably are surface crosslinked to improve absorbency characteristics. The poly(vinylamine) and acid resin combination behaves like an SAP in the presence of water, and especially brackish water. The poly(vinylamine) can be prepared by the improved method disclosed herein, or by prior methods known in the art. Crosslinking and surface crosslinking can be performed as set forth above.

The poly(vinylamine) is a basic resin that is admixed with an acidic resin. The acidic resin can be any resin that acts as an SAP in its neutralized form. The acidic resin typically contains a plurality of carboxylic acid, sulfonic acid, phosphonic acid, phosphoric acid, or sulfuric acid moieties, or a mixture thereof.

Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylenemaleic anhydride copolymers, isobutylene-maleic anhydride copolymers, poly(vinylsulfonic acid), poly(vinylsulfuric acid), poly(vinylphosphoric acid, sulfonated polystyrene, poly(vinylphosphonic) acid, and mixtures thereof. The preferred acidic resins are the polyacrylic acids.

The poly(vinylamine) is present in its uncharged, i.e., free base, form, and the acidic resin is present in its free acid form. It is envisioned that a low percentage, i.e., 25% or less, of the amine and acid functionalities can be in their charged form, due to processing, for example. The low percentage of charged functionalities does not adversely affect performance of the superabsorbent material, but the amount of charged functionalities should be minimized.

The poly(vinylamine) and acidic resin are admixed in a weight ratio of about 5:95 to about 95:5, and preferably about 10:90 to about 90:10. To achieve the full advantage of the present invention, the resins are admixed in a weight ratio of about 30:70 to about 70:30. A present bi-component SAP material is prepared by simply admixing particles of the poly(vinylamine) and acidic resin to provide a uniform particulate material To illustrate a present bi-component SAP material, the following examples were prepared and tests performed:

EXAMPLE 7

Powdered poly(vinylamine), as prepared in Example 5 (particle size 210–710 μm) was admixed with lightly crosslinked polyacrylic acid (particle size 210–710 μm, 0% neutralized) in a weight ratio of 37% poly(vinylamine) to 63% polyacrylic acid. The absorbency characteristics of the resulting bi-component SAP were tested and compared to the absorbency characteristics with respect to a 0.9% by weight aqueous NaCl solution. The results are set forth in Table 4.

TABLE 4

| | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(vinyl-amine)/ Polyacrylic Acid Blend | 21.2 | 18.6 | 28.3 | 23.8 | 20.5 | 36.3 |
| Poly(vinyl-amine) | 14.2 | 14.4 | 21.4 | 15 | 14.3 | 23.4 |

Table 4 shows that the poly(vinylamine)/polyacrylic acid blend has substantially improved absorption properties compared to poly(vinylamine) alone.

The bi-component SAP materials are especially useful in articles designed to absorb and retain liquids, especially electrolyte-containing liquids. Such articles include, for example, diapers and catamenial devices.

To illustrate the improved absorption properties of a bi-component SAP material of the present invention, the blends described in the following Table 5 were prepared and tested for an ability to absorb synthetic urine under a 0.7 psi load. As used here and throughout the specification, poly (AA) (DN=70) refers to a standard, commercial poly(AA) neutralized about 70% to about 80%, and poly(AA) (DN=0) refers to unneutralized poly(AA).

TABLE 5

| Example | Blend Ratio[5] | AUL 0.7 psi (1 hr) | AUL 0.7 psi (3 hr) |
|---|---|---|---|
| 1[1] | 75/25 | 27.1 | 28.9 |
| 1 | 50/50 | 30.9 | 33 |
| 1 | 25/75 | 35.9 | 40.2 |
| 2[2] | 75/25 | 26.6 | 27.3 |
| 2 | 50/50 | 28.7 | 30.3 |
| 2 | 25/75 | 26.3 | 27.3 |
| 3[3] | 75/25 | 25.3 | 26 |
| 3 | 50/50 | 21.3 | 22.8 |
| 3 | 25/75 | 15.7 | 16.4 |
| 4[4] | 55/45 | 37 | 45.2 |

[1]Blend of (a) partially neutralized poly(AA)-(DN = 70) and (b) a mixture containing 55% by weight poly(vinylamine) and 45% by weight poly(AA) (DN = 0);
[2]Blend of (a) partially neutralized poly(AA)-(DN = 70) and (b) poly (vinylamine);
[3]Blend of (a) partially neutralized poly(AA)-(DN = 70) and (b) poly(AA) (DN = 0);
[4]Blend of (a) poly(vinylamine) and (b) poly(AA)-(DN = 0); and
[5]Weight ratio of (a) to (b) in each blend.

The data presented in Table 5 shows a substantial improvement in absorption properties achieved by a bi-component SAP material of the present invention, either when used alone (i.e., Example 4) or in combination with a standard SAP material, like poly(AA) (DN=70) (i.e., Example 1).

To further illustrate that the present bi-component SAP materials have an improved ability to absorb and retain liquids compared to a present-day SAP, laboratory diaper cores containing a present bi-component SAP material were prepared and compared to laboratory diaper cores containing a conventional SAP. In particular, the following the diaper cores were prepared:

Core A1—50% poly(AA) (DN=70) and 30% fluff
Core A2—70% poly(AA) (DN=70) and 50% fluff
Core B—27.5% poly(vinylamine), 22.5% poly(AA) (DN=0), and 50% fluff pulp, by weight,
Core C—identical to Core B except the poly(vinylamine) was surface crosslinked with 500 ppm EGDGE,
Core D—38.5% poly(vinylamine), 31.5% poly(AA) (DN=0), and 30% fluff pulp, by weight,
Core E—identical to Core D except the poly(vinylamine) was surface crosslinked with 500 ppm EGDGE.

Typically, commercial diapers contain 45% to 60% by weight of a pulp to achieve rapid absorption of a liquid. Diaper Cores A through E were compared to one another to illustrate the improved permeability and absorption rate, and improved liquid absorption and retention, provided by a diaper having a core that contains a bi-component SAP material of the present invention.

Present day diapers generally consist of a topsheet made from a nonwoven material that is in contact with the skin of the wearer, an acquisition layer below (i.e., opposite the skin of wearer) the topsheet, a core that is below the acquisition layer, and a backsheet below the core. This construction is well known in the industry.

Cores A through E were prepared using a conventional laboratory procedure as follows:

A laboratory core-forming unit comprising a two-chamber vacuum system forms an airlaid fluff pulp-absorbent composite matrix to produce a 12 cm×21 cm diaper core. The core-forming unit comprises a roller brush on a variable-speed laboratory motor, a fiber distribution screen in close proximity to the brush, a forming screen on an adjustable damper, and a vacuum system capable of supplying a consistent and continuous negative pressure between 8 and 15 inches of water.

The core-forming unit is contained such that the vacuum pulls the fibers and granular material from an adjustable introduction slide, through the rotating brush and distribution screen, directly onto the forming screen. The vacuum exhaust is recirculated through the inlet of the formation slide, thereby controlling the temperature and humidity of the operation.

When forming a core, the desired amount of defiberized fluff pulp is evenly disbursed in small pieces onto the brush roller in the upper chamber. In the lower chamber, a rectangular tissue, or topsheet (21 cm×12 cm), is placed onto the forming screen. For most cores, the sliding upper chamber lid is partially closed to leave about a one-half inch gap. In the case of a homogeneous pulp/SAP core, the SAP is sprinkled through the gap into the upper chamber immediately after the brush begins rotating. In order to achieve a homogeneous distribution, a small amount of SAP is added to the fluff prior to beginning the motor. The amount of time used to introduce the remainder of the SAP varies with the amount of fluff pulp utilized. After the fiber and absorbent polymer material are deposited, the motor is turned off, and the damper unit containing the laboratory core is removed from the lower chamber. The uncompressed core then is placed on a backsheet made from a polymeric film, and put into a compression unit. At this time, another rectangular tissue and a nonwoven coverstock is placed on top of the core. Absorbent cores are compressed for a given amount of time, typically 5 minutes, with a hydraulic press at pressures of between about 5,000 psi and about 10,000 psi, and typically about 7,000 psi, to achieve the desired density. After the 5 minutes, the laboratory-prepared absorbent cores are removed from the press, weighed, and measured for thickness.

Cores A through H2, and other laboratory cores and commercial diapers, were tested for rewet under a 0.7 psi load, liquid acquisition time, and liquid acquisition rate. The following describes the procedure to determine the acquisition and rewet under load of a hygienic article, like a diaper. These tests exhibit the rate of absorption and fluid retention of a 0.9%, by weight, saline solution, by a hygienic article over 3 to 5 separate fluid insults while under a load of 0.7 psi.

Apparatus 100 ml separatory funnel, configured to deliver a flow rate of 7 ml/sec., or equivalent;

3.642 kg circular weight (0.7 psi) 10 cm diameter, with 2.38 cm ID perspex dose tube through the center of weight;

VWR Scientific, 9 cm filter paper or equivalent;

2.5 kg circular weight (0.7 psi)-8 cm diameter;

Digital timer;

Electronic balance (accuracy of a 0.01 gram);

Stopwatch.

Procedure

1. Preparation (a) Record the weight (g) of the hygienic article, e.g., diaper, to be tested;

(b) Place hygienic article flat on the bench top, for example, by removing any elastics and/or taping the ends of the article to the bench top;

(c) Place the 3.64 kg circular weight onto the hygienic article with the opening of the perspex dose tube positioned at the insult point (i.e., 5 cm toward the front from the center).

2. Primary Insult and Rewet Test (a) Measure 100 ml of 0.9% NaCl solution (i.e., 0.9% by weight sodium chloride in deionized or distilled water) into separatory funnel. Dispense the NaCl solution into the perspex tube of the weight at a flow rate of 7 ml/sec and start the timer immediately. Stop the timer when all of the NaCl solution has completely disappeared from the surface of the hygienic article at the base of the perspex tube. Record this time as the primary acquisition time (sec).

(b) After 10 minutes have elapsed, remove the weight and conduct the rewet test procedure:

(i) Weigh a stack of 10 filter papers, record this value (dry weight).

(ii) Place the filter papers over the insult point on the hygienic article. Set the timer for 2 minutes. Place the 2.5 kg weight onto the filter papers and start timer immediately.

(iii) After 2 minutes have elapsed, remove the weight and reweigh the filter papers (wet weight). Subtract the dry weight of the filter papers from the wet weight, this is the rewet value. Record this value as the primary rewet value (g).

3. Secondary Insult and Rewet Test (a) Place the 3.64 kg weight back onto the hygienic article in the same position as before. Repeat step 2a using 50 ml NaCl solution (recoding the absorption time as the secondary acquisition time) and steps 2b (i)–(iii) using 20 filter paper (recording the rewet values as the secondary rewet).

4. Tertiary, and additional, Insult and Rewet Tests (a) Place the load back onto the diaper in the same position as before. Repeat step 2a using 50 ml of NaCl solution (recording the absorption time as the tertiary acquisition time) and steps 2b (i)–(iii) using 30 filter paper (recording the rewet value as the tertiary or subsequent rewet).

FIGS. 1–4 illustrate the improved properties of diapers that contain a bi-component SAP material of the present invention.

FIG. 1 contains plots of acquisition time vs. number of insults with 0.9% aqueous saline, under a 0.7 psi load, for diapers containing Cores A1, B, and C. In FIG. 1, Cores B and C are cores of the present invention. Core A1 is a comparative core.

Cores B and C exhibited an excellent ability to acquire 0.9% saline under a 0.7 psi load. Core A1 acquired the saline relatively slowly, especially during rewetting. Core A1 represents a standard core containing 50% SAP, and has a higher acquisition time than Cores B or C. The acquisition time for Core A1 could not be measured beyond the fourth insult because acquisition was very slow.

Figure 2:
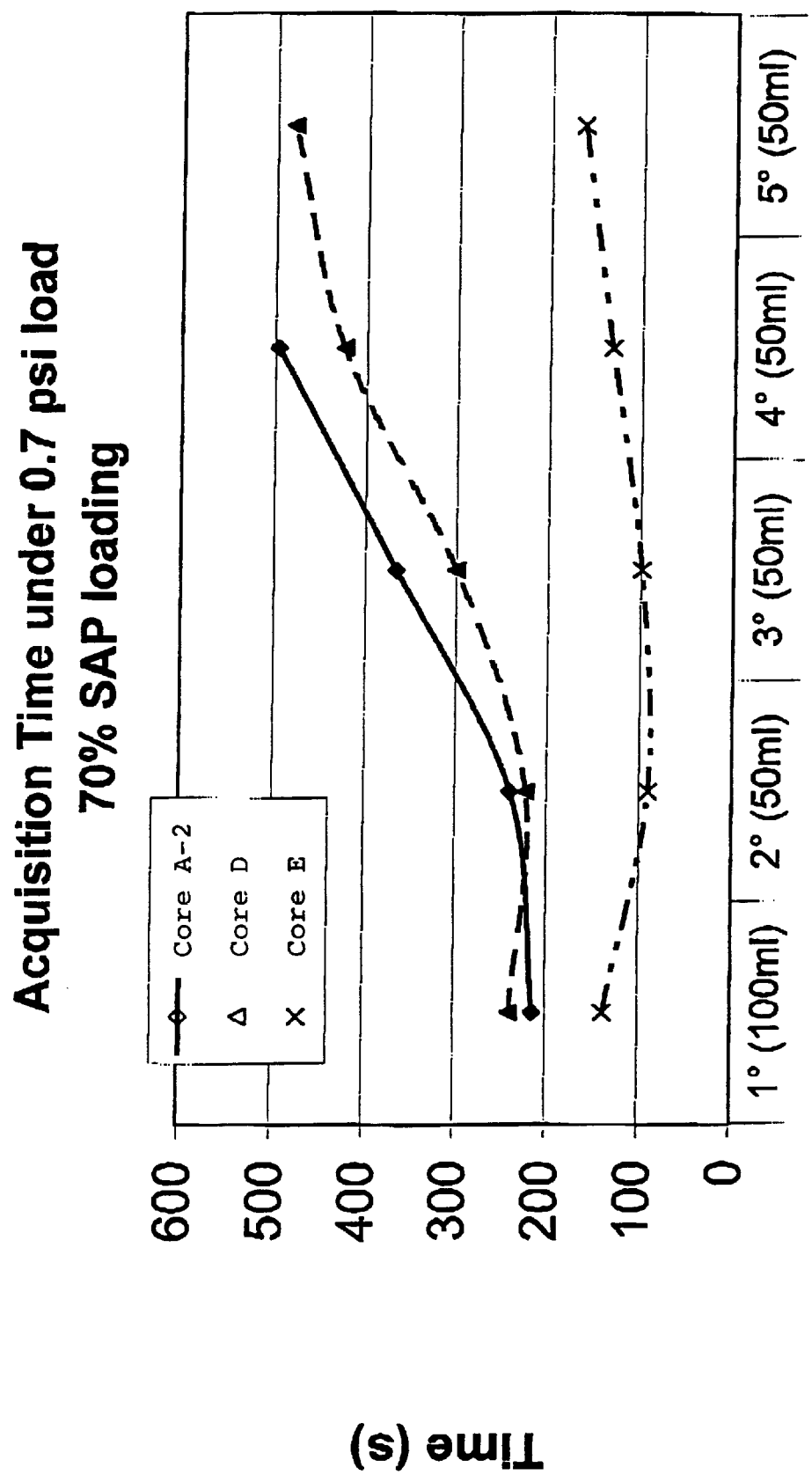

FIG. 2 illustrates the acquisition time for Cores A2, D, and E. FIG. 2 shows that Cores D and E, i.e., cores of the present invention, significantly outperform a comparative laboratory core (Core A2) with respect to acquisition time of 0.9% saline under a 0.7 psi load.

Figure 3:
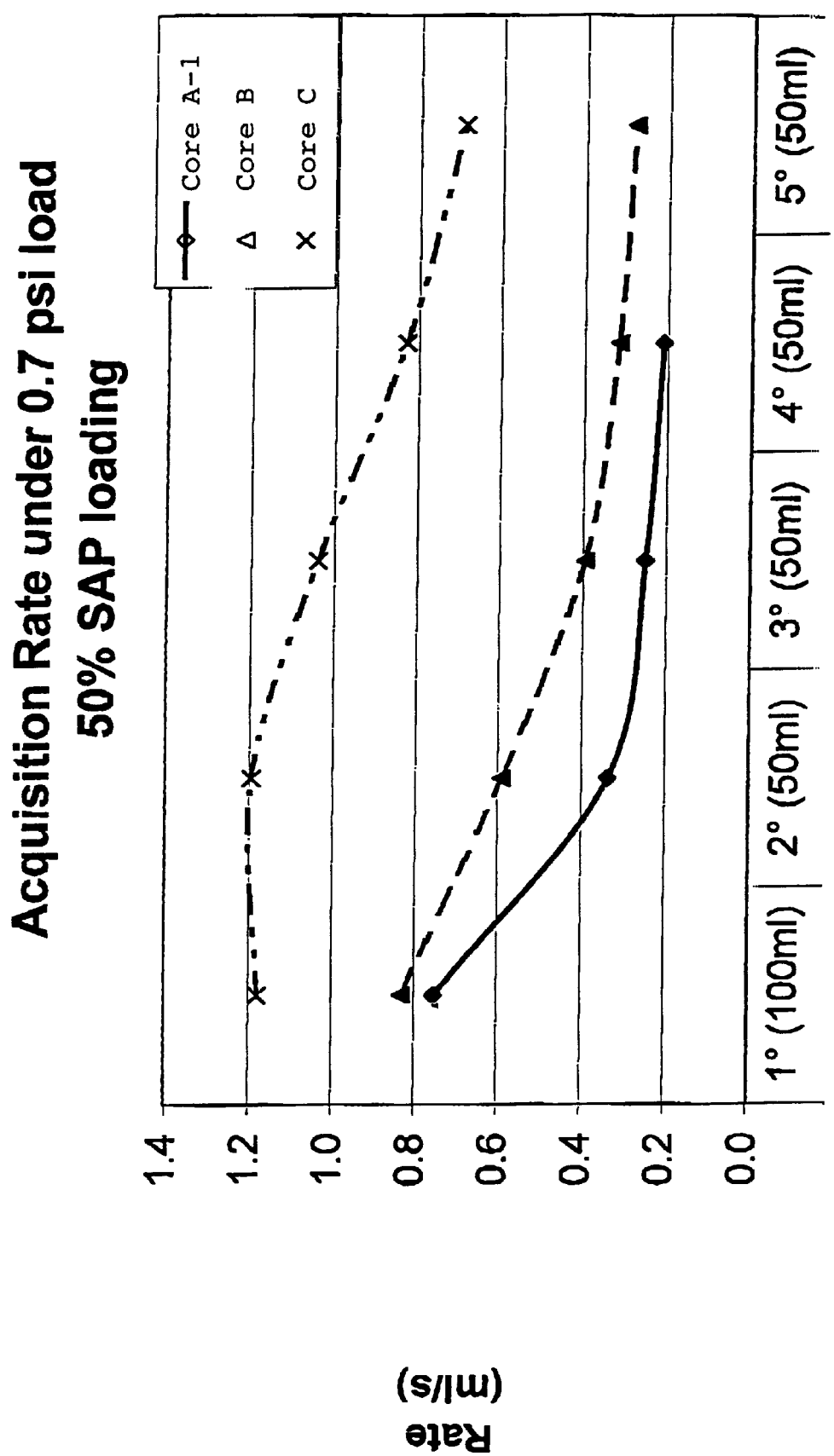
FIGS. 3 and 4 are plots of acquisition rate (ml/sec) vs. number of insults for a series of laboratory prepared diaper cores under a load of 0.7 psi.
Figure 4:
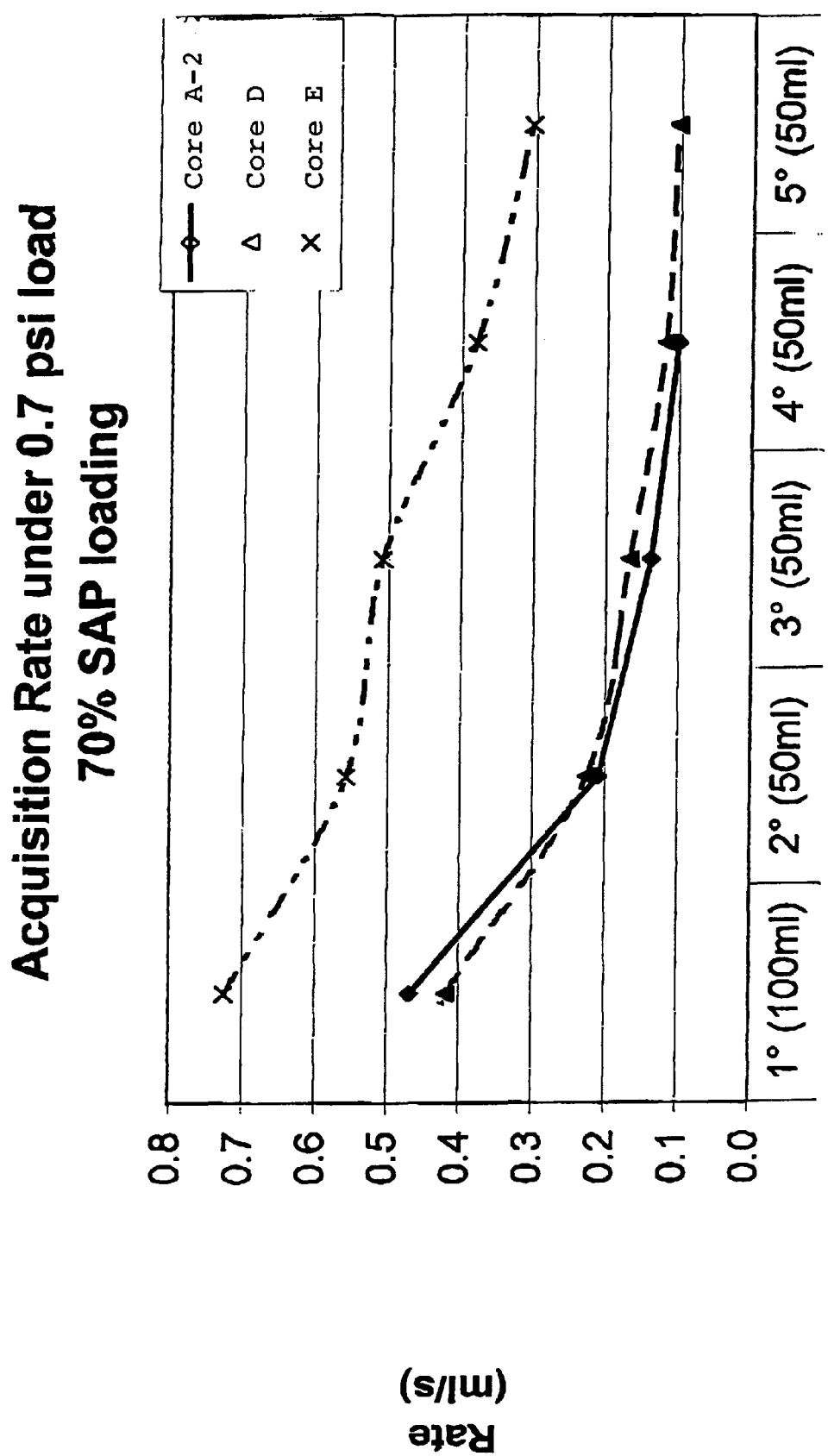

FIGS. 3 and 4 illustrate that a core of the present invention, i.e., Cores B–E, have a greater acquisition rate than comparative laboratory cores containing poly(AA) (DN=70).

Overall, the data presented in FIGS. 1–4 demonstrate that a diaper core of the present invention maintains a flat, essentially constant, or surprisingly a decreased, acquisition time over five insults, whereas prior cores demonstrate an increased acquisition time over prior cores. The data also shows an improved acquisition rate as the number of insults increases. Such results are unexpected because prior cores exhibit a decrease in acquisition rate as the number of insults increase, especially between the first and second insult. The present cores maintain the initial acquisition rate after a second insult with saline (see FIG. 3). The present cores, therefore, can have a second acquisition rate that is at most 20% slower than a first acquisition rate, and preferably is at least equal to the first acquisition rate. The practical result of these improved properties is a core having an improved ability to prevent leakage in gush situations and in rewet situations.

The data shows that improvements in liquid absorption, both with respect to kinetics and retention, are observed if the standard poly(AA) (DN=70) presently used in cores is completely replaced by bi-component SAP material of the present invention.

The improved results demonstrated by a core of the present invention also permit the thickness of the core to be reduced. Typically, cores contain 50% or more fluff or pulp to achieve rapid liquid absorption while avoiding problems like gel blocking. The present cores, which contain a bi-component SAP material, acquire liquids sufficiently fast to reduce problems, like gel blocking, and, therefore, the amount of fluff or pulp in the core can be reduced. A reduction in the amount of the low-density fluff results in a thinner core, and, accordingly, a thinner diaper.

Cores containing as little as about 25% by weight of a bi-component SAP material demonstrate an excellent ability to absorb and retain liquids. Preferably, a core of the present invention contains at least 50% of a bi-component SAP material, and most preferably at least 75% of a bi-component SAP material. The bi-component SAP material can be used alone in the core, or in combination with fluff and/or standard SAP particles, like poly(AA) (DN=70). The bi-component SAP material can be admixed with the fluff and/or standard SAP particles for introduction into a diaper core. Alternatively, the diaper core can contain zones of bi-component SAP particles and zones of standard SAP particles.

Many modifications and variations of the invention as hereinbefore set forth can be made without departing from the spirit and scope thereof and, therefore, only such limitations should be imposed as are indicated by the appended claims.

What is claimed is:

1. A diaper having a core, said core comprising at least 25% by weight of a superabsorbent material comprising
    (a) a lightly crosslinked poly(vinylamine), and
    (b) an acidic water-absorbing resin selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphoric acid), a sulfonated polystyrene, a poly(vinylphosphonic acid), and mixtures thereof,
    wherein the poly(vinylamine) and the acidic resin are present in a weight ratio of about 5:95 to about 95:5, and the poly(vinylamine) is neutralized 0 to 25% and the acidic water-absorbing resin is neutralized 0 to 25%.

2. The diaper of claim 1 wherein the core comprises at least 50% by weight of the superabsorbent material.

3. The diaper of claim 1 wherein the core comprises at least 75% by weight of the superabsorbent material.

4. The diaper of claim 1 wherein the core further comprises an acidic water-absorbing resin neutralized from 25 to 100%.

5. The diaper of claim 4 wherein the neutralized acidic water-absorbing resin is poly(acrylic acid).

6. The diaper of claim 1 wherein the core has an acquisition rate for absorbing 100 milliliters of 0.9% saline under a load of 0.7 psi of greater than one milliliter/second.

7. The diaper of claim 6 wherein the core has an acquisition rate for absorbing a subsequent 50 milliliters of 0.9% saline of greater than 0.8 milliliter/second.

8. The diaper of claim 1 further comprising a topsheet in contact with a first surface of the core, and a backsheet in contact with a second surface of the core, said second core surface opposite from said first core surface.

9. The diaper of claim 8 further comprising an acquisition layer disposed between the topsheet and the core.

10. The diaper of claim 1 wherein the poly(vinylamine) is surface crosslinked.

11. The diaper of claim 10 wherein the poly(vinylamine) is surface crosslinked with up to about 1% of a surface crosslinking agent, by weight of the poly(vinylamine).

12. The diaper of claim 10 wherein the surface crosslinker comprises ethylene glycol diglycidyl ether.

13. The diaper of claim 1 wherein the poly(vinylamine) and the acidic resin are present in a weight ratio of about 20:80 to about 80:20.

14. The diaper of claim 1 wherein the poly(vinylamine) and the acidic resin are present in a weight ratio of about 35:65 to about 65:35.

15. The diaper of claim 1 wherein the poly(vinylamine) is a homopolymer.

16. The diaper of claim 1 wherein the poly(vinylamine) comprises vinylamine and at least one additional monoethylenically unsaturated monomer.

17. A diaper having a core, said core comprising at least 25% by weight of a superabsorbent material comprising
    (a) a lightly crosslinked poly(vinylamine), and
    (b) an acidic water-absorbing resin selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphoric acid), a sulfonated polystyrene, a poly(vinylphosphonic acid), and mixtures thereof,
    wherein the core has an acquisition rate for absorbing 100 milliliters of 0.9% saline under a load of 0.7 psi of greater than one milliliter/second, and the poly(vinylamine) is neutralized 0 to 25% and the acidic water-absorbing resin is neutralized 0 to 25%.

18. The diaper of claim 17 wherein the core has an acquisition rate for absorbing a subsequent 50 milliliters of 0.9% saline of greater than 0.8 milliliter/second.

19. A diaper having a core, said core comprising at least 25% by weight of a superabsorbent material comprising
   (a) a lightly crosslinked poly(vinylamine), and
   (b) an acidic water-absorbing resin selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphoric acid), a sulfonated polystyrene, a poly(vinylphosphonic acid), and mixtures thereof,
   wherein the poly(vinylamine) is surface crosslinked with up to about 1% of a surface crosslinking agent, by weight of the poly(vinylamine), and wherein the poly(vinylamine) is neutralized 0 to 25% and the acidic water-absorbing resin is neutralized 0 to 25%.

20. The diaper of claim 19 wherein the surface crosslinker comprises ethylene glycol diglycidyl ether.

21. A diaper having a core, said core comprising at least 25% by weight of a superabsorbent material comprising
   (a) a lightly crosslinked poly(vinylamine), and
   (b) an acidic water-absorbing resin selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphoric acid), a sulfonated polystyrene, a poly(vinylphosphonic acid), and mixtures thereof,
   wherein the poly(vinylamine) comprising vinylamine and at least one additional monoethylenically unsaturated monomer, and wherein the poly(vinylamine) is neutralized 0 to 25% and the acidic water-absorbing resin is neutralized 0 to 25%.

* * * * *